United States Patent [19]
Collis, Jr.

[11] Patent Number: 4,527,787
[45] Date of Patent: Jul. 9, 1985

[54] X-RAY TABLE

[76] Inventor: John S. Collis, Jr., 29001 Cedar Rd., Cleveland, Ohio 44124

[21] Appl. No.: 499,538

[22] Filed: May 31, 1983

[51] Int. Cl.³ .............................................. A61G 13/00
[52] U.S. Cl. .................................... 269/322; 378/208
[58] Field of Search .................... 269/17, 60, 322–325, 269/328; 378/208, 209

[56] References Cited

U.S. PATENT DOCUMENTS

| | | | |
|---|---|---|---|
| 1,194,112 | 8/1916 | Wood | 269/322 |
| 2,568,191 | 9/1951 | Grimm | 378/208 |
| 2,700,583 | 1/1955 | Davis et al. | 269/325 |
| 3,197,198 | 7/1965 | Collis | 378/209 X |
| 3,783,863 | 1/1974 | Kliever | 269/328 |

Primary Examiner—Frederick R. Schmidt
Assistant Examiner—Judy J. Hartman Attorney, Agent, or Firm—Pearne, Gordon, Sessions, McCoy, Granger & Tilberry

[57] ABSTRACT

A medical table which can be used for examination of the spine and for other diagnostic and therapeutic back procedures, including discography and surgery, and which can be adapted for use with imaging devices, has a bottom support frame, a front support frame resting on the front of the bottom support frame, and a rear support frame resting on the bottom support frame. The front and rear support frames are spaced from each other to provide a substantial clearance for imaging devices including radiographic and fluoroscopic apparatus. A radiolucent top panel is supported at one end by the front support frame and at the other end by the rear support frame. The use of front and rear support frames rather than side support frames eliminates radiopaque material adjacent to the top panel and permits oblique, lateral, as well as anterioposterior views to be taken.

12 Claims, 10 Drawing Figures

X-RAY TABLE

BACKGROUND OF THE INVENTION

1. Field of the Invention

This invention relates to a medical table for examination of the spine and for other diagnostic and therapeutic back procedures, and more particularly to a table which is adapted for use with an imaging device.

2. Description of the Prior Art

Tables of this type are used for various surgical and other medical procedures, such as lumbar and thoracic discography, including the injection of enzymes, cortisone, procaine or other analgesics, and contrast media. Such tables may also be used for electromyography, electrostimulation, proctology, rhizolysis and various other procedures.

When such tables are used for discography, electromyography, and other procedures in which injections are being performed or when probes or electrodes are being inserted, it is necessary that the location of the injection, probe, or electrode be precise in order to avoid the nerve bundles which are adjacent to the spine. Fluoroscopy, or some other imaging technique, may be used to monitor the position of the injection, probe, or electrode so that it can be performed precisely.

Recently, the use of chymopapain has been approved for injection into the lumbar discs to relieve the problems associated with herniated discs. As this procedure becomes more popular, the use of such surgical tables may increase.

U.S. Pat. No. 3,197,198, issued to John S. Collis, describes such a medical table in which the patient-supporting table top had a convex surface, so that when the patient was placed on the table, the patient's spine was in a maximally flexed condition. The table top was supported by a pair of side frames, one on each side. Each side frame consisted of a vertical forward leg and a forwardly inclined rearward leg which was longer than the forward leg. An upper side rail joined the two legs together and extended along the top of the table to complete the side frame. The patient was positioned on the table, with the patient's knees resting on a vertically adjustable platform. The adjustment of the platform was operated by a handwheel located at the front of the table which was connected to the platform by a rotatable rod which extended across the table beneath the table top.

While the medical table described in U.S. Pat. No. 3,197,198 represented a substantial improvement over previous tables, it had several disadvantages. The table was entirely suitable for making anterioposterior radiological images, but presented problems when taking lateral views and was unsatisfactory for taking oblique views because of the construction of the side frame. The side frame, which included a member running across the top of the table, was radiopaque and produced a shadow in views taken other than anterioposteriorally. In lateral views, the side frames produced a shadow which, depending upon the positioning of the patient, might not interfere with observation of the spine. However, in oblique views, the shadow produced by the side frame could interfere with a clear observation of the spine. Thus, oblique radiological views were not practical using this table, and tomography was very difficult or impossible.

Another problem with the aforementioned table was in the operation of the adjustable knee platform. Although the vertically adjustable knee platform was a convenience in adjusting the patient properly on the table top, the operating handwheel was located at the front of the table, which was inconvenient to the physician and the medical attendants who judged the positioning of the patient at the rear end of the table. Thus, it was necessary for the physician or the medical attendants to observe the positioning of the patient on the table, to walk around to the front of the table to adjust the handwheel and subsequently to return to the back of the table to reposition the patient. This procedure was often repeated several times before the patient was properly positioned on the table. In addition, the rotatable rod which connected the handwheel to the adjusting mechanism for the knee platform extended longitudinally across the length of the table and could possibly interfere with the portion of an imaging device which was placed beneath the table top.

SUMMARY OF THE INVENTION

The present invention overcomes the problems of the prior art tables and provides other advantages heretofore not attainable.

The present invention avoids the problems of the side frame construction of the medical table in the aforementioned patent by replacing the dual side frame construction with a front frame structure and a rear frame structure so that there are no side members extending longitudinally along the table which could produce undesirable radiological shadows. Thus, the medical table of the present invention provides a radiolucent table top which is supported only at its ends by a front frame structure and a rear frame structure. There is no support for the table top along either side, and thus there is no radiopaque side frame to produce undesirable shadows.

The table of the present invention is particularly well adapted for surgical and other medical procedures which use fluoroscopic or other image monitoring during the procedure, such as lumbar and thoracic discography. When injecting the patient with enzymes, cortisone, procaine or other analgesic, or with contrast media for certain diagnostic purposes, it is necessary that the needle be placed precisely, and for this reason it is often necessary to simultaneously use an imaging device to observe the interior positioning of the needle during the injection. Such imaging devices are often positioned to take views obliquely or laterally so as not to interfere with the injection itself. An oblique view is preferable since it shows positioning of the needle in two dimensions. By providing a support frame which does not need side members along each side of the table top, a clear, oblique radiographic or fluoroscopic image can be obtained. Indeed, images can be made or tomography can be performed in oblique planes and lateral planes, as well as in anterioposterior planes, without worrying about placement of the imaging apparatus with regard to the support structure of the table.

In addition, the medical table of the present invention includes a knee platform which is vertically adjustable, and in which the operational element of the adjustment is located at the rear of the table adjacent to the position of the physician or other medical personnel who would be adjusting the patient. Thus, it is not necessary to move to the front of the table to operate the adjustable knee platform and then return to the rear of the table to reposition the patient.

By locating the operational element of the knee platform at the rear of the table, the adjusting mechanism is located entirely at the rear end of the table, and there are no mechanical elements extending longitudinally across the table, which elements may interfere with the placement of an imaging device beneath the center of the table top.

These and other advantages are achieved by the medical table of the present invention. The table comprises a bottom support frame. A front support frame rests on the bottom support frame and is attached thereto.

A rear support frame, which is spaced from the front support frame, is also supported on the bottom support frame and attached thereto. There is a substantial clearance between the front frame and the rear frame so that an imaging device may be placed therebetween.

A radiolucent top panel is supported at one end by the front support frame and at the other end by the rear support frame. The panel has a generally convex upper surface having a raised center portion and end portions which are inclined downwardly to the support points. The presence of radiopaque material between the front support frame and the rear support frame is thereby avoided.

In accordance with another aspect of the invention, a vertically adjustable knee platform is mounted on the rear support frame and is operatively connected to a cranking member which is also located on the rear support frame.

DETAILED DESCRIPTION OF THE PREFERRED EMBODIMENT

Figure 1:
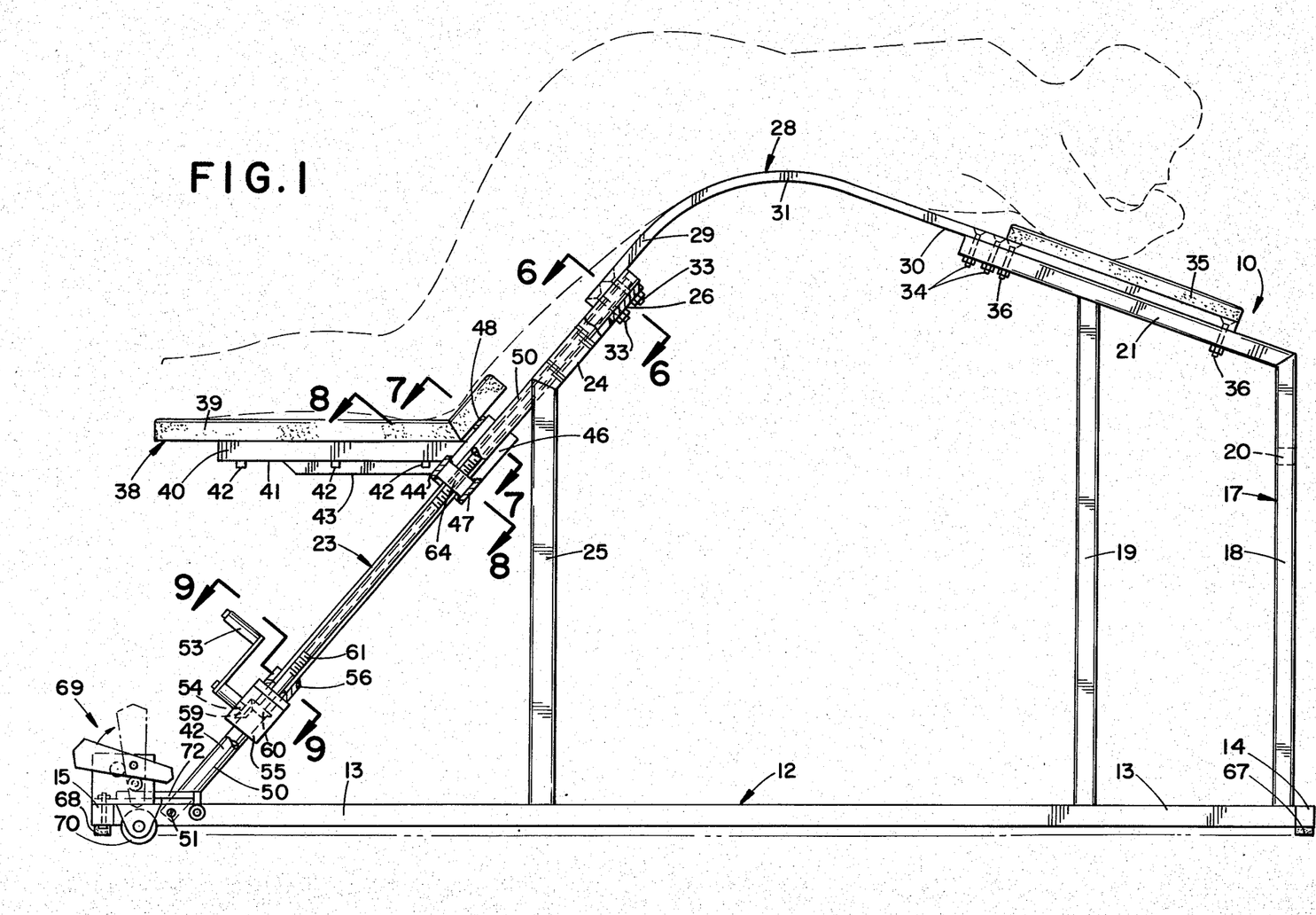
FIG. 1 is a side elevational view of the medical table of the present invention, showing in phantom lines the position of a patient on the table.
Figure 2:
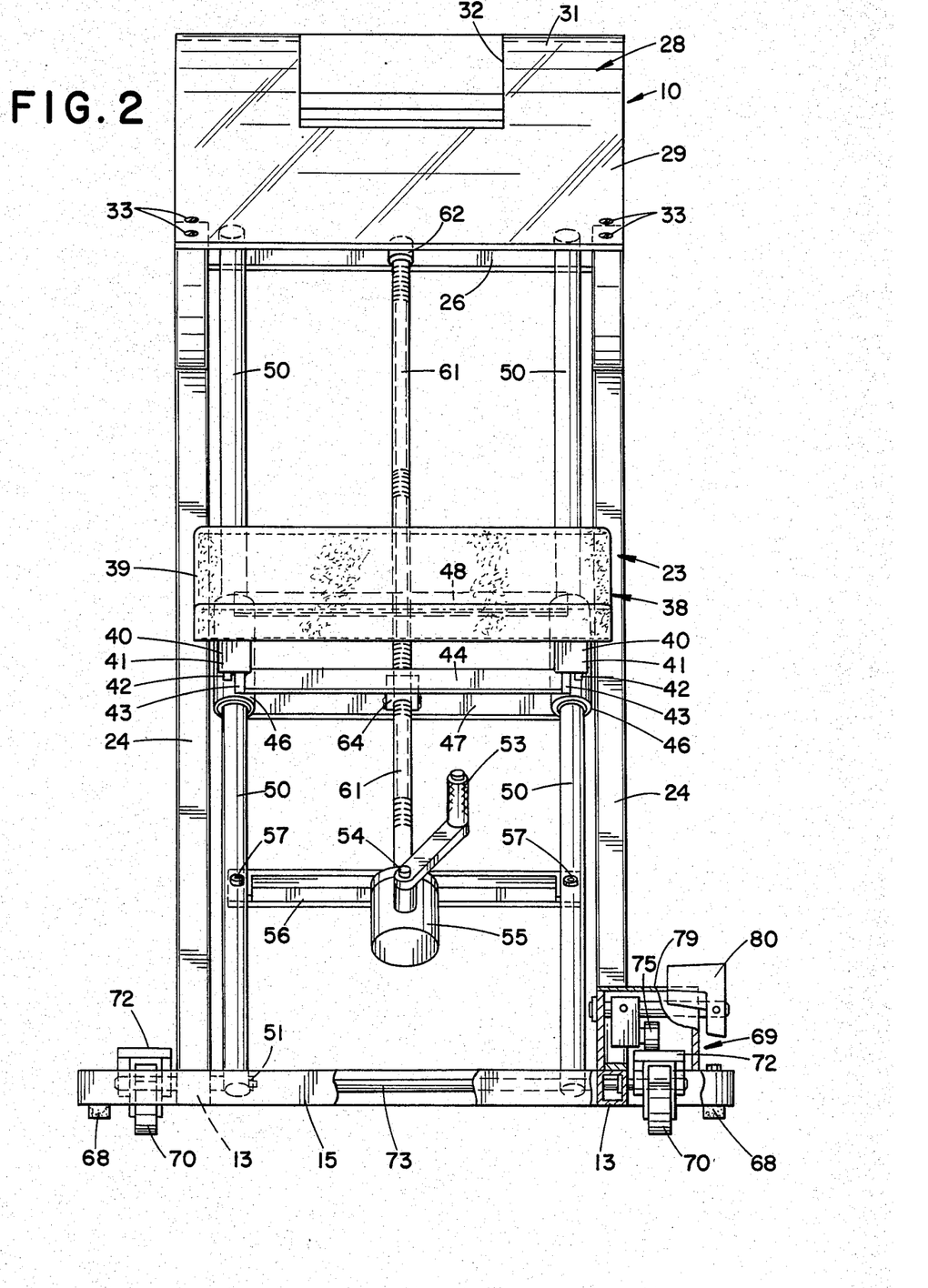
FIG. 2 is a rear, elevational view of the table of FIG. 1.
Figure 3:
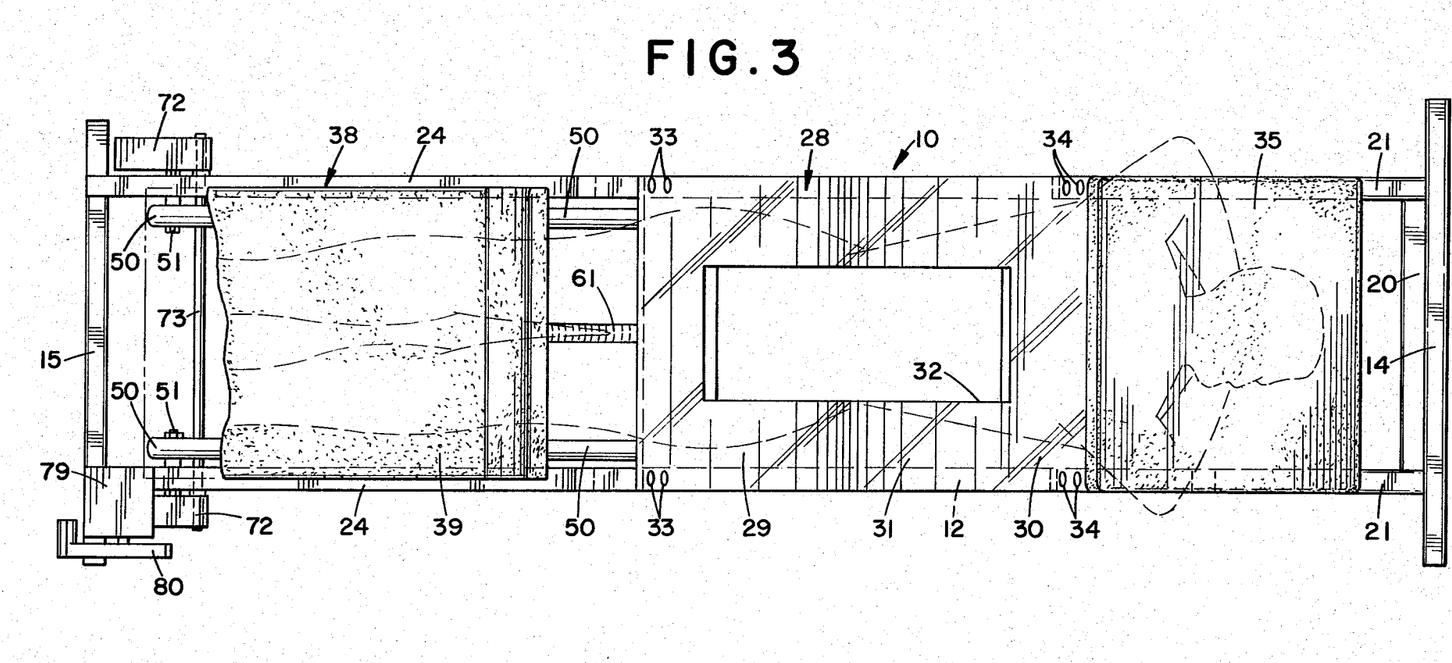
FIG. 3 is a top plan view of the table of FIG. 1.
Figure 4:
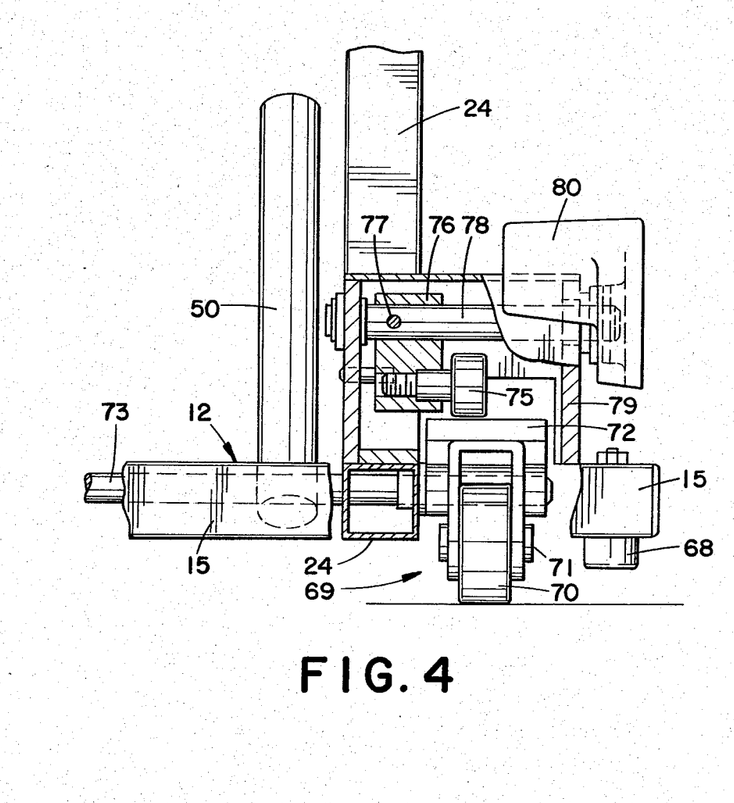
FIG. 4 is a detailed end elevational view of a portion of the table shown in FIG. 2 to a larger scale.
Figure 5:
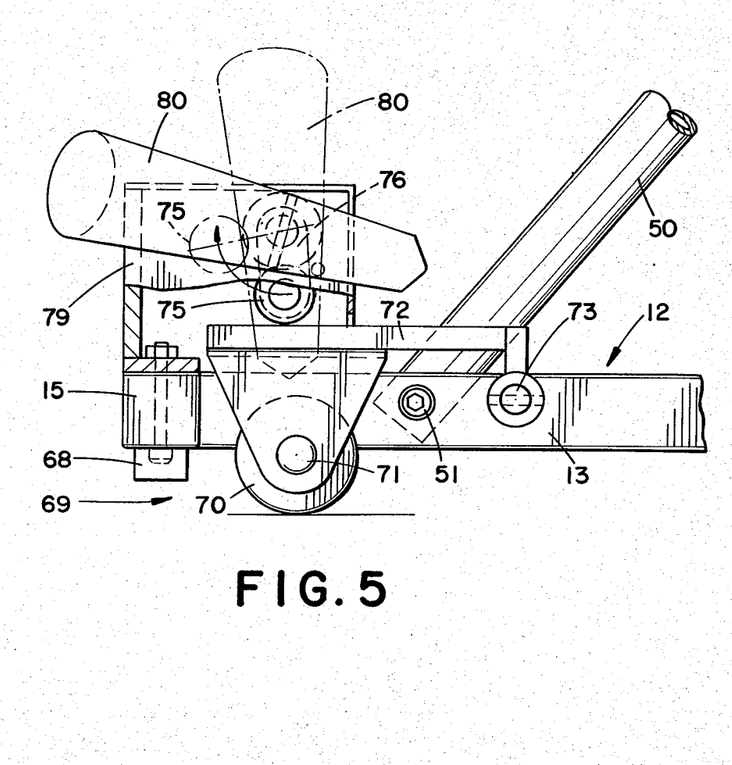
FIG. 5 is a side elevational view of the table portion of FIG. 4 shown to a larger scale than in FIG. 1.
Figure 6:
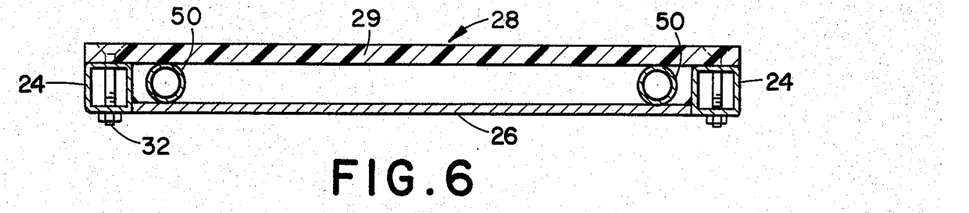
FIG. 6 is a cross-sectional view, taken along line 6—6 of FIG. 11.
Figure 7:
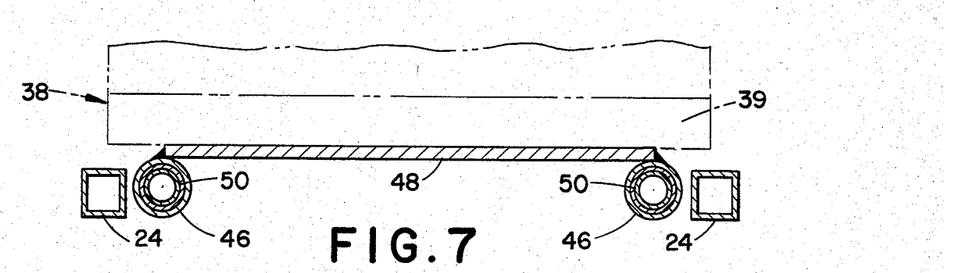
FIG. 7 is a cross-sectional view, taken along line 7—7 of FIG. 1.

Referring more particularly to the drawings, and initially to FIGS. 1-3, there is shown a medical table 10 made in accordance with the present invention. The table 10 comprises a generally rectangular bottom frame 12 formed of a pair of bottom side frame members 13 connected together at the front of the table by a bottom front frame member 14 and connected together at the rear of the table by a bottom rear frame member 15.

At the front end of the table, a front support frame 17 rests on the bottom support frame 12 and is attached thereto. The front support frame 17 is formed of a pair of front upright frame members 18 located at each front corner of the table and a pair of second upright frame members 19 spaced behind the front upright frame members 18. The second upright frame members 19 are slightly longer than the front upright frame members 18. A cross frame member 20 extends between the two front upright frame members 18 near the top of the table to provide rigidity to the front support frame 17. The front support frame 17 also includes a pair of front top frame members, each supported on one of the front upright frame members 18 and one of the second upright frame members 19. Since the second upright frame members 19 are slightly longer than the front upright frame members 18, the front top frame members 21 incline upwardly away from the front of the table.

At the rear end of the table, a rear support frame 23 is supported on the bottom support frame 12 and is attached thereto. The rear support frame 23 comprises a pair of inclined rear frame members 24 which extend upwardly from the rear corners of the table. The rear frame members 24 are both inclined toward the front of the table and form an angle of approximately 60° with respect to the bottom side frame members 13. A pair of second upright frame members 25 are supported on the bottom side frame members 13 in front of the inclined rear frame members 24. The second upright frame members 25 extend at a right angle with respect to the bottom side frame members 13 so that the upper portion of the rear frame members 24 are supported on top of the upright frame members 25. The inclined rear frame members 24, the upright frame members 25, and the rear end of the bottom side frame members 13 form a rigid, triangular, rear support frame, as shown in FIG. 1. A rear cross frame member 26 extends across between the upper ends of the inclined rear frame members 25 to increase the rigidity of the rear frame.

A generally convex table top panel 28 is supported at one end by the front support frame 17, and at the other end by the rear support frame 23. The panel 28 is formed of a radiolucent material, i.e., a material which is pervious to X-rays, gamma rays, or the like, and which is sufficiently strong to support the weight of the patient, and may be readily cleaned. A suitable material for the top panel 28 is Lucite.

The top panel 28 includes a generally flat rear portion 29 upon which the upper thighs of the patient will rest, a generally flat front portion 30 upon which the chest of the patient will rest, and a curved intermediate portion 31 upon which the pelvic region of the patient will rest. A rectangular opening 32 may be provided in the intermediate portion 31, through which the patient's abdomen may extend which maintaining the desired spinal curvature. The rear portion 29 of the top panel 28 is attached at each side to the upper ends of the rear frame members 24 and to the cross frame member 26 by means of fasteners 33, such as bolt and nut assemblies. The front portion 30 of the top panel is attached at each side to the rearward ends of the front top frame members 21 by means of fasteners 34, such as bolt and nut assemblies. It has been found that for optimal positioning of patients on the medical table of the present invention the rear portion 29 of the top panel should make an angle of approximately 90° with respect to the front portion 30 of the top panel, and that the radius of curvature of the intermediate portion 31 should be approximately 10.5 inches (26.7 cm).

A front cushion 35 is provided for resting the patient's shoulders and elbows. The front cushion 35 is attached at each side to the front top frame members 21 by means of fasteners 36, which may also be bolt and nut assemblies.

The patient's knees are supported on an adjustable knee rest 38 which extends horizontally behind the rear support frame 23. The knee rest 38 comprises the cushion 39 mounted on top of a horizontally extending platform 40. The platform 40 comprises a pair of horizontally extending rails 41 to which the cushion 39 is attached by means of fasteners 42. A horizontally extending bar 43 extends beneath each rail 41 and is attached thereto. A cross bar 44 extends between the bars 43 and is supported at each end by attachment to one of the bars 43. The cross bar 44 is supported at each end by attachment to a tubular bushing 46. Each bushing 46 is slidably mounted on a rod 50 which extends parallel to and just inside of one of the rear frame members 24. The bottom end of each rod 50 is attached to one of the bottom side frame members by a pin 51. The upper end of the rod is attached to the rear cross frame member 26.

Another cross bar 47 extends parallel to and spaced from the cross bar 44 beneath the bushings 46. The cross bar 47 is supported at each end by attachment to the bushings 46. The platform 40 also includes a cross bar 48 attached at each end to the bushings 46 on the same side of the bushings as the cross bar 44. The cross bar 48 supports the upper portion of the cushion 39 which extends parallel to the rear frame member 24.

The knee rest 38 is vertically adjusted by an adjusting mechanism operated by means of a crank 53 located at the rear of the table behind the frame 23. The crank 53 rotates a shaft 54 which is journaled in a gear box 55. The gear box 55 is mounted beneath an L-shaped cross bar 56 which extends between the two rods 50. Each end of the cross bar 56 is mounted to one of the rods 50 by a fastener 57.

Figure 8:
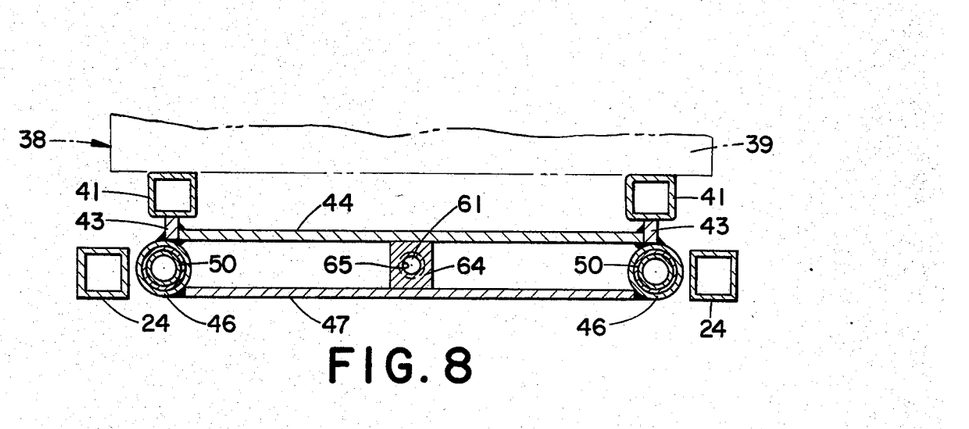
FIG. 8 is a cross-sectional view, taken along line 8—8 of FIG. 1.
Figure 9:
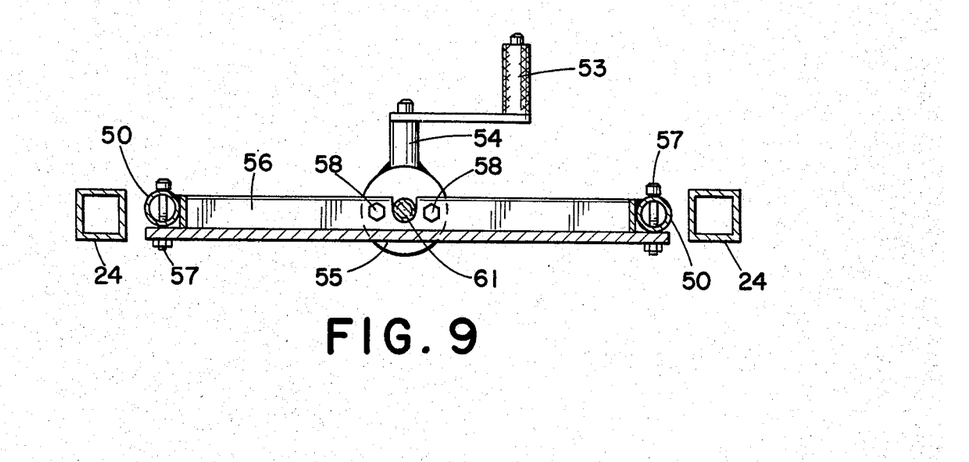
FIG. 9 is a cross-sectional view, taken along line 9—9 of FIG. 1.

Within the box 55, a bevel gear 59 is mounted on the end of the crankshaft 54. The bevel gear 59 engages a corrresponding bevel gear 60 located on the bottom of a threaded rod 61 which is located between the rods 50 and extends parallel thereto. The upper end of the threaded rod 61 extends through an opening in the rear cross frame member 26, and a collar 62 is mounted on the upper end of the threaded rod 61 above the rear cross frame member 26 to support the threaded rod. A positioning block 64 has a central threaded opening 65 (FIG. 8) in which the threaded rod 61 extends. The positioning block 64 is mounted between the cross bars 44 and 47. The threaded rod 61 engages the threaded opening 65, so that the positioning block 64 moves up and down as the rod 61 rotates.

The knee rest 38 is adjusted by turning the crank 53. As the crank 53 turns, it rotates the shaft 54 and the attached bevel gear 59. The bevel gear 59 engages the bevel gear 60 which, in turn, rotates the threaded rod 61. The threaded rod 61, which engages the threaded opening 65 on the positioning block 64, causes the positioning block 64 to move up and down as the rod 61 rotates. The block 64 is fixed between the cross bars 44 and 47, which form part of the platform 40 for the knee rest 38, so that as the block 64 moves up and down, the platform 40 moves up and down while being fully supported by engagement of the bushings 46 around the rods 50.

The table 10 is supported on feet 67 and 68 located at each corner of the bottom support frame 12. The front feet 67 are located at each end of the bottom frame member 14. The rear feet 68 are located at each end of the bottom rear frame member 15.

The table may be made more readily movable by means of a retractible wheel assembly 69 located at the rear of the table along the bottom rear frame member 15. The wheel assembly 69 comprises a pair of wheels 70 each mounted by means of an axle 71 in a wheel support 72. Each wheel support 72 is pivotally attached to one of the bottom side frame members 13 by means of a rod 73. The rod 73 extends across the table parallel to and in front of the bottom rear frame member 15, and is connected to both wheel supports 72. The pivotal wheel supports 72 are free to pivot upwardly so that the bottom support frame 12 of the table moves downwardly with respect to the wheel assembly 69 and the rear of the bottom support frame rests on the rear feet 68. The wheel supports 72 may also be moved downwardly to raise the bottom support frame 12 upwardly with respect to the wheel support, so that the rear of the table is supported on the wheels 70 and not upon the rear feet 68. One of the wheel supports 72 is held in its downward position by a cam 75 mounted within a block 76. The block 76 is fixed by means of a pin 77 on a rotatable shaft 78. The shaft 78 is journaled within a housing 79 located over one of the wheels 70 and supported on a portion of the bottom rear frame member 15, which extends outwardly beyond the rear frame member 24. On the end of the shaft 78 outside of the housing 79 is an operational lever 80.

To retract the wheel assembly 69 so that the rear of the table rests on the rear feet 68, the lever 80 is moved from the generally horizontal position to a vertical position, such as by actuation by a foot, rotating the shaft 78 and pivoting the block 76 which is mounted on the shaft. As the block 76 pivots, the cam 75 is moved out of engagement with the top of one of the wheel supports 72. The wheel support 72 thus moves upwardly and pivots about its mounting on the rod 73. The rod 73, which extends across the table, rotates to pivot the other wheel support 72 upwardly as well.

When it is desired to move the table, the wheel assembly 69 can be moved back down by moving the lever 80 from the vertical position back to the generally horizontal position, turning the shaft 78, pivoting the block 76, and moving the attached cam 75 such that it pushes the top of one of the wheel supports 72 downwardly with respect to the bottom support frame 12 to raise the support frame upwardly so that the rear of the table rests on the wheel 70. As the wheel support 72 which is engaged by the cam 75 moves downwardly, the rod 73 rotates, moving the other wheel support 72 downwardly as well. To move the table, the front of the table is lifted, such as by means of the front cross frame member 20, and the table is moved on the rear wheels 70. Since the majority of the weight of the table is in the rear of the table, including the positionable knee rest 38, the table may be readily moved in this fashion.

Figure 10:
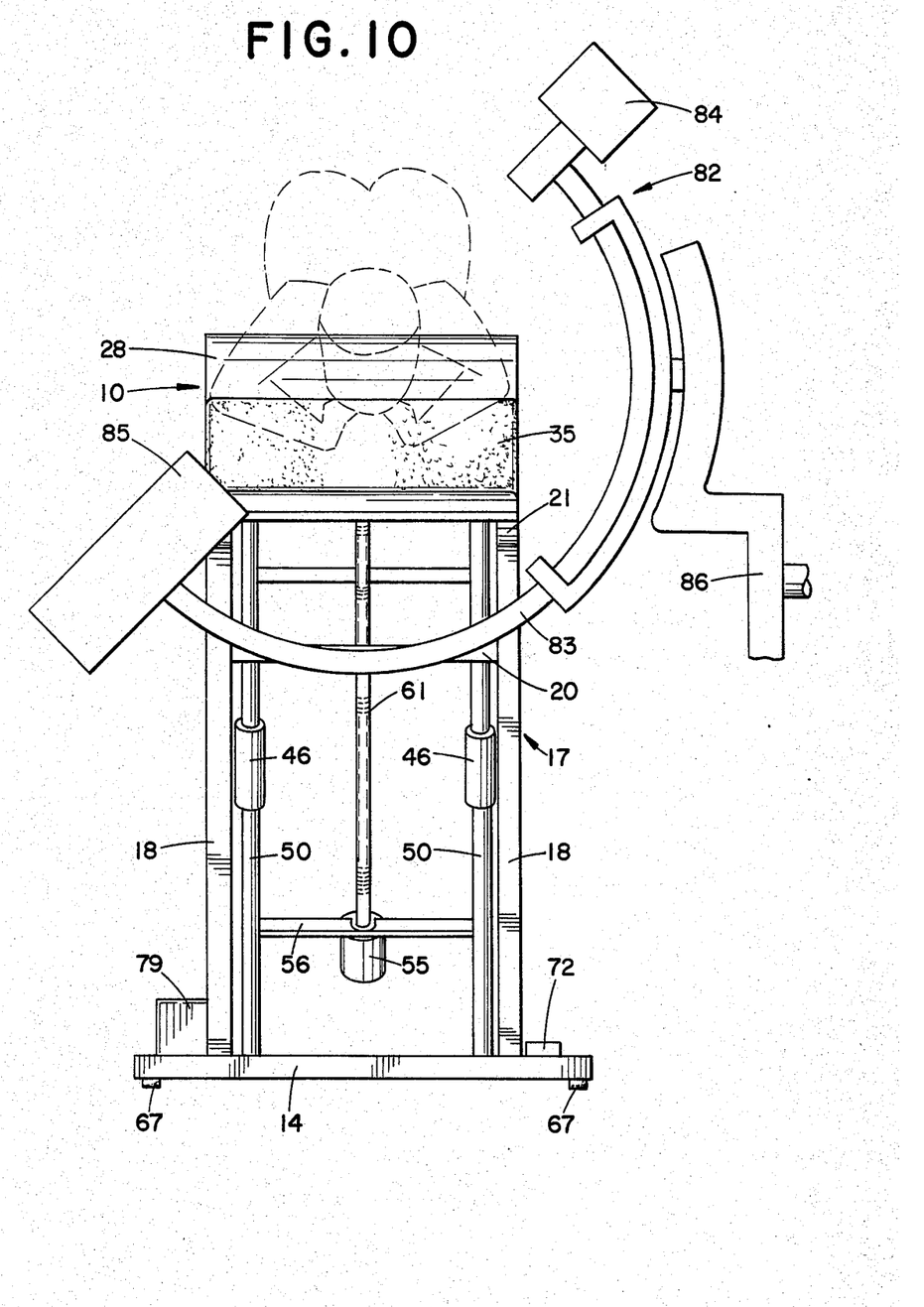
FIG. 10 is a front elevational view of the table of FIG. 1 showing the table used in combination with an imaging device.

The table of the present invention is readily adapted for use with a multitude of imaging devices in order to perform surgical or other medical procedures. An imaging device may be a diagnostic radiographic unit, or it may be a fluoroscopic unit that is used to create a radiograph or a fluoroscopic image. Imaging devices need not be limited to radiographic or fluoroscopic units. They can include ultrasound or other equipment which may or may not be used in conjunction with data processing systems. Radiographic or fluoroscopic devices which deliver x-rays obliquely, laterally or anteroposteriorally can be used with the table of the present invention to perform tomographic or other radiographic procedures. A fluroscopic unit 82 that is equipped with an image intensifier and a means for transmitting an image to a video monitor, or a holder that contains x-ray sensitive film (a cassette or a camera) is shown in FIG. 10. The unit 82 includes a C-shaped arm 83 and an x-ray emitter 84 at one end, and it includes an apparatus 85 for creating as well as for transmitting an image at the other end. The ionizing radiation emitter 84 is typically an x-ray tube. The apparatus 85 may be an image intensifier and a television camera (as shown in FIG. 10), or it may be a cassette or a camera which contains film that is sensitive to X-radiation.

The C-arm 83 is adjustably mounted on the end of a horizontal extending support 86 which is in turn attached to the base of the image intensifier (not shown). The C-arm 83 may be moved along the support 86 into any desired position, including a position in which the emitter 84 is on one side of the table and the imaging device 85 is on the other side of the table to obtain lateral views, and a position in which the emitter 84 is over the table and the imaging device 85 is in the middle of the table beneath the top panel 28 and between the front support frame 17 and the rear support frame 23 to obtain anterioposterior views. As shown in FIG. 10, the C-arm 83 is positioned to obtain an oblique view.

It will be noted that the front support frame 17 is spaced from the rear support frame 23 so that it is possible to position the radiographic or fluoroscopic device therebetween, and that adequate space is provided for such an imaging device. Furthermore, since the front support frame 17 is spaced away from the rear support frame 23, there is no radiopaque support frame to interfere with radiographic or fluoroscopic images taken obliquely or laterally through the table top panel 28.

While the invention has been shown and described with respect to a particular embodiment thereof, this is for the purpose of illustration rather than limitation, and other variations and modifications of the specific embodiment herein shown and described will be apparent to those skilled in the art all within the intended spirit and scope of the invention. Accordingly, the patent is not to be limited in scope and effect to the specific embodiment herein shown and described nor in any other way that is inconsistent with the extent to which the progress in the art has been advanced by the invention.

What is claimed is:

1. A medical table comprising:
   a bottom support frame having a front and a rear;
   a front support frame resting on the bottom support frame and attached thereto, the front support comprising a pair of first upright frame members supported on the first of the bottom support frame, a pair of second upright frame members extending generally parallel to the front upright frame members and spaced behind the front upright frame members, and a pair of front top frame members each supported on top of one of the first upright frame members and one of the second upright frame members;
   a rear support frame spaced from the front support frame, the rear support frame also resting on the bottom support frame and attached thereto, there being a substantial clearance between the front support frame and the rear support frame; and
   a radiolucent top panel supported at a front end by the front support frame and at a rear end by the rear support frame, the front end of the top panel being supported by attachment to the front top frame members, the panel being generally convex in shape with an intermediate raised portion, thetop of the front support frame being connected to the top of the rear support frame only by the radiolucent top panel without any radiopaque connection therebetween, whereby the presence of radiopaque material between the front support frame and the rear support frame is avoided.

2. A medical table as set forth in claim 1, comprising in addition a cushion supported on top of the front support frame for resting the patient's upper body.

3. A medical table as set forth in claim 1, wherein the convex top panel has a radius of curvature of approximately 10 inches.

4. A medical table as set forth in claim 1, wherein the rear portion of the top panel forms an angle with respect to the front portion of the top panel of approximately 90°.

5. A medical table comprising:
   a bottom support frame having a front and a rear;
   a front support frame resting on the bottom support frame and attached thereto;
   rear support frame spaced from the front support frame, the rear support frame also resting on the bottom support frame and attached thereto, the rear support fram comprising a pair of rear frame members extending from the rear of the bottom support frame at an acute angle with respect thereto, and a pair of upright frame members in front of the rear frame members, an upper portion of each of the rear frame members being supported on top of one of the upright frame members, there being a substantial clearance between the front support frame and the rear support frame; and
   a radiolucent top panel supported at a front end by the front support frame and at a rear end by the rear support frame, the rear end of the top panel being supported by attachment to the rear frame members, the panel being generally convex in shape with an intermediate raised portion, the top of the front support frame being connected to the top of the rear support frame only by the radiolucent top panel without any radiopaque connection therebetween, whereby the presence of radiopaque material between the front support frame and the rear support frame is avoided.

6. A medical table as set forth in claim 5, comprising in addition a knee rest attached to the rear support frame.

7. A medical table as set forth in claim 6, wherein the knee rest is vertically adjustable on guide rails located on the rear support frame.

8. A medical table as set forth in claim 7, comprising in addition operating means for moving the adjustable knee rest vertically, the operating means being located on the rear support frame and being operational from the rear of the medical table.

9. A medical table as set forth in claim 8, wherein the operational element is a hand crank supported on the rear support frame, the hand crank turning a threaded rod extending parallel to the rear support frame, the knee rest being supported on a platform having a block with a threaded opening through which the threaded rod extends, whereby turning the crank rotates the threaded rod to move the block up and down and vertically adjust the knee rest.

10. A medical table as set forth in claim 5, wherein the acute angle is approximately 60°.

11. A medical table as set forth in claim 5, comprising in addition a retractable wheel assembly located beneath the rear of the bottom support frame.

12. A medical table as set forth in claim 11, wherein the retractable wheel assembly is operated by means of an operational element located on one side of the bottom support frame, the operational element retracting wheels on both sides of the bottom support frame.

* * * * *

UNITED STATES PATENT AND TRADEMARK OFFICE
CERTIFICATE OF CORRECTION

PATENT NO. : 4,527,787
DATED : July 9, 1985
INVENTOR(S) : John S. Collis, Jr.

It is certified that error appears in the above-identified patent and that said Letters Patent are hereby corrected as shown below:

Column 3, line 43, "FIG. 11" should be --FIG. 1--.

Column 7, line 55, "front" should be --first--.

Column 8, line 3, "thetop" should be --the top--.

Column 8, line 27, "fram" should be --frame--.

Signed and Sealed this

Fifteenth Day of October 1985

[SEAL]

Attest:

Attesting Officer

DONALD J. QUIGG

Commissioner of Patents and Trademarks—Designate